US012054515B2

United States Patent
Chen et al.

(10) Patent No.: US 12,054,515 B2
(45) Date of Patent: Aug. 6, 2024

(54) CORN PROTEIN ISOLATE AND METHODS OF MANUFACTURING SAME

(71) Applicant: Cargill, Incorporated, Wayzata, MN (US)

(72) Inventors: Yumin Chen, Gurnee, IL (US); Eugene Max Peters, Jr., Kettering, OH (US); Michael A. Porter, Maple Grove, MN (US); Craig A. Wilson, Sidney, OH (US); Guo-Hua Zheng, Centerville, OH (US); Hadi Nayef Yehia, Beavercreek, OH (US)

(73) Assignee: CARGILL, INCORPORATED, Wayzata, MN (US)

(*) Notice: Subject to any disclaimer, the term of this patent is extended or adjusted under 35 U.S.C. 154(b) by 238 days.

(21) Appl. No.: 15/560,866

(22) PCT Filed: Mar. 24, 2016

(86) PCT No.: PCT/US2016/024020
§ 371 (c)(1),
(2) Date: Sep. 22, 2017

(87) PCT Pub. No.: WO2016/154441
PCT Pub. Date: Sep. 29, 2016

(65) Prior Publication Data
US 2018/0118780 A1    May 3, 2018

Related U.S. Application Data

(60) Provisional application No. 62/137,526, filed on Mar. 24, 2015.

(51) Int. Cl.
C07K 1/14       (2006.01)
A23J 1/00       (2006.01)
(Continued)

(52) U.S. Cl.
CPC .............. *C07K 1/14* (2013.01); *A23J 1/006* (2013.01); *A23J 1/16* (2013.01); *C07K 14/415* (2013.01); *C08H 1/00* (2013.01); *C08B 30/044* (2013.01)

(58) Field of Classification Search
None
See application file for complete search history.

(56) References Cited

U.S. PATENT DOCUMENTS 2,105,760 A * 1/1938 Swallen ............... C07K 14/425
530/373
2,120,946 A    6/1938 Swallen
(Continued)

FOREIGN PATENT DOCUMENTS

CN       1899076 A     1/2007
CN     101560252 A    10/2009
(Continued)

OTHER PUBLICATIONS

Anderson "Detoxification of Aflatoxin-Contaminated Corn", Proc. Symp. held in Atlanta, Ga., Jan. 26-27, 1982. South. Coop. Ser. Bull. 279:87-90 (Year: 1982).*
(Continued)

*Primary Examiner* — Felicia C Turner

(57) ABSTRACT

Aspects of the present invention provide a corn protein isolate, comprising at least about 85 wt % corn protein on a dry basis; an "a*" color value ranging from about −0.5 and 1.5, and a "b" color value ranging from about 10 and 25; and less than about 1.5% oil on a dry basis. Further aspects include methods of making the same.

14 Claims, 2 Drawing Sheets

(51) Int. Cl.
   *A23J 1/16*     (2006.01)
   *C07K 14/415*   (2006.01)
   *C08H 1/00*     (2006.01)
   *C08B 30/04*    (2006.01)

(56)           References Cited

U.S. PATENT DOCUMENTS

| | | | |
|---|---|---|---|
| 2,124,284 A * | 7/1938 | Bole | C08B 30/042 |
| | | | 127/27 |
| 2,133,591 A | 10/1938 | Swallen | |
| 2,156,928 A | 5/1939 | Swallen | |
| 2,218,221 A | 10/1940 | Schopmeyer | |
| 2,227,605 A * | 1/1941 | Swallen | B01D 11/023 |
| | | | 422/268 |
| 2,360,381 A | 10/1944 | Walsh | |
| 2,384,388 A | 9/1945 | Nicholas | |
| 2,414,195 A | 1/1947 | Evans | |
| 2,704,257 A | 3/1955 | De Sollano | |
| 4,018,936 A * | 4/1977 | Garbutt | A23J 3/18 |
| | | | 426/430 |
| 4,024,120 A | 5/1977 | Phillips | |
| 4,108,847 A | 8/1978 | Creinin | |
| 4,213,941 A * | 7/1980 | Boomer | B01D 11/023 |
| | | | 422/267 |
| 4,265,925 A | 5/1981 | Campbell | |
| 4,361,651 A | 11/1982 | Keim | |
| 4,624,805 A * | 11/1986 | Lawhon | A23J 1/12 |
| | | | 426/14 |
| 4,716,218 A | 12/1987 | Chen et al. | |
| 5,254,673 A * | 10/1993 | Cook | C07K 14/425 |
| | | | 426/656 |
| 5,254,763 A | 10/1993 | Gill | |
| 5,367,055 A * | 11/1994 | Takahashi | A23J 1/12 |
| | | | 426/656 |
| 5,410,021 A | 4/1995 | Kampen | |
| 5,498,431 A | 3/1996 | Lindner | |
| 5,510,463 A | 4/1996 | Takahashi | |
| 5,580,959 A | 12/1996 | Cook et al. | |
| 5,602,286 A | 2/1997 | Muralidhara | |
| 5,798,446 A | 8/1998 | Neumuller | |
| 5,847,238 A | 12/1998 | Muralidhara | |
| 6,169,217 B1 | 1/2001 | Cheryan | |
| 6,433,146 B1 | 8/2002 | Cheryan | |
| 6,602,985 B1 | 8/2003 | McInnis et al. | |
| 6,610,831 B1 | 8/2003 | McInnis et al. | |
| 6,846,909 B2 | 1/2005 | Mairal et al. | |
| 7,045,607 B2 | 5/2006 | Cheryan | |
| 7,829,680 B1 | 11/2010 | Sander | |
| 8,795,760 B2 | 8/2014 | Lawton | |
| 9,226,515 B2 | 1/2016 | Van et al. | |
| 2001/0009040 A1 | 7/2001 | Duvick | |
| 2002/0183490 A1 | 12/2002 | Cheryan | |
| 2003/0066106 A1 | 4/2003 | Strissel et al. | |
| 2003/0198725 A1 | 10/2003 | Cardenas | |
| 2004/0009263 A1 | 1/2004 | Liu | |
| 2005/0008759 A1 | 1/2005 | Nie et al. | |
| 2005/0064079 A1 | 3/2005 | Allen et al. | |
| 2005/0074538 A1 | 4/2005 | Elder et al. | |
| 2006/0057275 A1 | 3/2006 | Wu | |
| 2006/0182857 A1 | 8/2006 | Thorre | |
| 2006/0240169 A1 | 10/2006 | Heydtmann et al. | |
| 2007/0087101 A1 | 4/2007 | Gusek et al. | |
| 2007/0172914 A1 | 7/2007 | Slabbekoorn et al. | |
| 2008/0102502 A1 | 5/2008 | Foody et al. | |
| 2008/0118626 A1 | 5/2008 | McWilliams | |
| 2009/0041901 A1 | 2/2009 | Elmusa et al. | |
| 2009/0053368 A1 | 2/2009 | Fox et al. | |
| 2009/0148589 A1 | 6/2009 | Fox et al. | |
| 2009/0209423 A1 | 8/2009 | Slabbekoorn | |
| 2009/0215990 A1 | 8/2009 | Cheryan et al. | |
| 2010/0016554 A1 | 1/2010 | Cheryan | |
| 2010/0159521 A1 | 6/2010 | Cirakovic et al. | |
| 2010/0221387 A1 | 9/2010 | Cristianini et al. | |
| 2010/0233756 A1 | 9/2010 | Sunvold et al. | |
| 2012/0027890 A1 | 2/2012 | Cerne | |
| 2013/0273219 A1 | 10/2013 | Baier | |
| 2014/0123855 A1 | 5/2014 | Lawton et al. | |
| 2014/0161962 A1 | 6/2014 | Boebel et al. | |
| 2014/0193547 A1 | 7/2014 | Brown | |
| 2014/0220217 A1 | 8/2014 | Brown et al. | |
| 2014/0271928 A1 | 9/2014 | Rehage | |
| 2014/0303348 A1 | 10/2014 | Lawton | |
| 2014/0343259 A1 | 11/2014 | Bleyer et al. | |
| 2014/0356510 A1 | 12/2014 | Schweizer et al. | |
| 2015/0201647 A1 | 7/2015 | Fosdick | |
| 2016/0165932 A1 | 6/2016 | Armentrout | |
| 2016/0286840 A1 | 10/2016 | Shane | |
| 2017/0354737 A1 | 12/2017 | Harel et al. | |
| 2019/0029295 A1 | 1/2019 | Mielgo Iza et al. | |
| 2020/0236977 A1 | 7/2020 | Li et al. | |

FOREIGN PATENT DOCUMENTS

| | | |
|---|---|---|
| CN | 102037134 A | 4/2011 |
| CN | 101703146 B | 11/2011 |
| CN | 101560252 B | 1/2012 |
| CN | 102669406 A | 9/2012 |
| CN | 103059116 A | 4/2013 |
| CN | 103554278 A | 2/2014 |
| CN | 104938763 A | 9/2015 |
| CN | 105541982 A | 5/2016 |
| CN | 106009766 B | 11/2017 |
| EP | 0510537 A1 | 10/1992 |
| EP | 0648078 A1 | 4/1995 |
| EP | 2401920 A1 | 1/2012 |
| EP | 2491794 A1 | 8/2012 |
| EP | 3075259 A1 | 10/2016 |
| EP | 3375290 A2 | 9/2018 |
| FR | 2902607 A1 | 12/2007 |
| JP | 5754564 A | 4/1982 |
| JP | 63185998 A | 8/1988 |
| JP | 63185999 A | 8/1988 |
| JP | H06189687 A | 7/1994 |
| JP | H07179334 A | 7/1995 |
| JP | 2011097928 A | 5/2011 |
| JP | 4750901 B2 * | 8/2011 |
| KR | 101409213 B1 | 6/2014 |
| WO | 8809622 A1 | 12/1988 |
| WO | 9112730 A2 | 9/1991 |
| WO | 9312667 A1 | 7/1993 |
| WO | 9844807 A1 | 10/1998 |
| WO | 0150882 A2 | 7/2001 |
| WO | 2005074704 A1 | 8/2005 |
| WO | 2005091995 A2 | 10/2005 |
| WO | 2007019227 A1 | 2/2007 |
| WO | 2009155350 A1 | 12/2009 |
| WO | 2014186567 A1 | 11/2014 |
| WO | 2015004448 A1 | 1/2015 |
| WO | 2015109276 A1 | 7/2015 |
| WO | 2016154441 A1 | 9/2016 |
| WO | 2017011625 A1 | 1/2017 |
| WO | 2017040273 A3 | 4/2017 |
| WO | 2017058501 A1 | 4/2017 |
| WO | 2017081347 A2 | 5/2017 |
| WO | 2017165748 A1 | 9/2017 |
| WO | 2017165756 A1 | 9/2017 |
| WO | 2017189322 A1 | 11/2017 |
| WO | 2018058150 A1 | 3/2018 |
| WO | 2018237030 A1 | 12/2018 |
| WO | 2019028263 A2 | 2/2019 |
| WO | 2019060179 A1 | 3/2019 |
| WO | 2019060673 A1 | 3/2019 |

OTHER PUBLICATIONS

Takahara et al., JP4750901(B2)—English Translation, pp. 1-55. (Year: 2011).*

Reiners et al., "Corn Proteins: Potential for their Industrial Use" 58th Annual American Association of Cereal Chemists, 1973. (Year: 1973).*

(56) References Cited

OTHER PUBLICATIONS

Ivanova et al. "Producing of Feed protein concentrates as a method for rational utilization of recyclable fish material" Food processing Industry Issue Dec. 2011 abstract (Year: 2011).*

L Rey et al. Drugs and Pharmaceuticals Sciences "Freezing Drying Lyophilization of Pharmaceutical and Biological Products" Chap 1 2004 (Year: 2004).*

(International Standard ISO) Native starch—Determination of starch content—Ewers polarimetric method ISO 10520. Sep. 1997; p. 1, scope.

(Solvay Interox) "Hydrogen Peroxide Controlling reduced sulphur compounds" Mar. 2011; [retrieved May 25, 2017]. Retrived from the Internet: <URL:http://www.solvay.com.au/en/binaries/Controlling%20reduced%20suphur%20species-202502.pdf>.

Database WPI, Week 198219, Thomson Scientific, London, GB; AN 1982-38049E, XP002794657, & JP S 57 54564 A (Nippon Shokuhin Kako KK), Apr. 1, 1982 (Apr. 1, 1982).

Lawton, John W, "Zein: A History of Processing and Use", American Association of Cereal Chemists, Inc., vol. 79, No. 1, Jan. 18, 2002.

Lim, Ho-Soo , et al., "Comparison of four different methods for the determination of sulfites in foods marketed in South Korea", Food Additives & Contaminants: Part A, 3014, vol. 31, No. 2, 187-196, DOI: 10.1080/19440049.2013.857048.

Momany, Frank A., et al., "Structural Charecterization of a-Zein", Journal of Agricultural and Food Chemistry, 2006, 54, 543-547.

Phillips, R. Dixon, et al., "Corn Protein Concentrate: Functional and Nutritional Properties", Food Science, vol. 44, Issue 4 (Jul. 1979): pp. 1152-1155.

Sessa, David J., et al., "Improved Methods for Decolorizing Corn Zein", Industrial Crops and Products 18 (2003), 2003, 55-65.

Shukla, Rishi , et al., "Zein: the industrial protein from corn", Industrial Crops and Products 13 (2001), 171-192.

Wu, Y , et al., "balancing of sulfur storage in maize seed", BMC plant biology, vol. 12, May 30, 2012, 77: abstract; p. 3, figure 1; p. 8, col. 1, paragraph 2, May 2012, 3, 8.

Wu, Yv, et al., "Protein-Rich Residue from Corn Alcohol Distillation: Fractionation and Characterization", Cereal chemistry, vol. 58, No. 4, Apr. 1981, pp. 343-347.

McNeillie, Alastair, and Juli Bieser. "Hydrogen peroxide uses for the year 2000." Food Processing Oct. 1993: 59+. Business Insights: Global. Web. Feb. 9, 2016.

Anderson, Timothy J., et al., "Development of New Method for Extraction of a-Zein from Corn Gluten Meal Using Different Solvents", Cereal Chem. 88(4), 356-362.

Anderson, Timothy J., et al., "Zein Extraction from Corn, Corn Products, and Coproducts and Modifications for Various Applications: A Review", Cereal Chem. 88(2): 159-173, 2011.

Bryla, Marcin , et al., "Effects of pH and Temperature on the Stability of Fumonisins in Maize Products", Toxins 2017, 9, 88; doi:10.3390/toxins9030088.

Dickey, L.C. , "Ethanolic Extraction of Zein from Maize", Industrial Crops and Products 13 (2001), Apr. 30, 2000, 67-76.

Dombrink-Kurtzman , et al., "Effect of Nixtamalization (Alkaline Cooking) on Fumonisin-Contaminated Corn for Production of Masa and Tortillas", J. Agric. Food Chem., vol. 48(11): pp. 5781-5786, 2000.

Gomez, M. H., et al., "Changes in the Starch Fraction During Extrusion-cooking of Corn", Food Science, vol. 48, Issue 2 (Mar. 1983); pp. 378-381.

Hojilla-Evangelista, Mila P., et al., "Sequential Extraction Processing of High-Oil Corn", Cereal Chemistry, AACC International Inc., US, vol. 8, No. 6, Nov. 1, 2003 (Nov. 1, 2003), pp. 679-683, XP001185001, ISSN: 0009-0352.

Inglett, GE , et al., "high-shear, jet-cooking, and alkali treatment of corn distillers' dried grains to obtain products with enhanced protein, oil and phenolic antioxidants", food science and technology international, vol. 16, No. 4, Jul. 9, 2010, pp. 297-308; abstract; p. 298, col. 1, paragraph 5; p. 298, col. 2, paragraph 2; p. 300, table 2, Jul. 2010, 297-308.

Johansson, D , et al., "influence of surface lipids in commercial zein on microstructure and rheological properties of gluten-free dough", annual transactions of the nordic rheology society, vol. 20, 2012, pp. 247-251; p. 247, col. 1, paragraph 1; p. 247, col. 2, paragraph 4; p. 248, col. 1, paragraph 1; p. 248, figure 1, 2012, 247-251.

"The Corn Refining Process" 2 pages, downloaded fromn https://corn.org/wp-contentiuploads/2009/11/CornRefiningProcess.pdf (Year: 2009).

Anderson, R. A.; "Detoxification of Aflatoxin-Contaminated Corn", Cereal Chemistry, 55, 87-90, Jan. 31, 1978.

Anderson, Timothy James, "Extraction of zein from corn co-products", Master thesis, 2011, Food Science and Technology, Iowa State University, pp. i-v and 1-114.

Bookwalter Corn Distillers Grains and Other By-Products of Alcohol Production in Blended Foods. II. Sensory, Stability, and Processing Studies, Cereal Chem. vol. 61, No. 6, 1984, 509-513.

Burns TD et al: Fumonisin concentrations and in vivo toxicity of nixtamalized Fusarium verticillioides culture material: Evidence for fumonisin-matrix interactions, Food and Chemical Toxicology, Pergamon, GB, vol. 46, No. 8, Aug. 1, 2008 (Aug. 1, 2008), pp. 2841-2848, XP022939030, ISSN: 0278-6915, DOI: 10.1016/J.FCT.2008.05.017.

Gupta Ho et al: "Plant Foods for Human Nutrition 52: Processing of maize germ oil cake into edible food grade meal and evaluation of its protein quality", Plant Foods for Human Nutrition, vol. 52, Mar. 1, 1998 (Mar. 1, 1998), pp. 1-8, XP055808466, Retrieved from the Internet:URL:https://link.springer.com/content/pdf/10.1023/A:1008088822395.pdf>.

Hojilla-Evangelista MP et al: "Characterization of Protein Extracted From Flaked, Defatted, Whole Corn by The Sequential Extraction Process!", Journal of the American Oil Chemists Society, Springer, DE, vol. 69, No. 3, Mar. 1, 1992 (Mar. 1, 1992), pp. 199-204, XP000245384, ISSN: 0003-021X, DOI: 10.1007/BF02635886.

Johnson et al., "Optimizing Extraction of Zein and Glutelin-Rich Fraction During Sequential Extraction Processing of Corn", Cereal Chem. vol. 80, No. 4, 2003, 481-484.

Parris Net al: "Extraction and Solubility Characteristics of Zein Proteins From Dry-Milled Corn", Journal of Agricultural and Food Chemistry, American Chemical Society, US, vol. 49, No. 8, Aug. 1, 2001 (Aug. 1, 2001) , pp. 3757-3760, XP001071383, ISSN: 0021-8561, DOI: 10.1021/JF0011790.

Paulson et al. (1984) Can. Inst. Food Sci. Technol. J. 17:202-208.

Selling et al: "The effect of extrusion processing on Zein", Polymer Degradation and Stability, Bark I NG, GB, vol. 95, No. 12, Dec. 1, 2010 (Dec. 1, 2010), pp. 2241-2249, XP027527379, ISSN: 0141-3910.

Sydenham et al. J. Agric. Food Chem. 1995, vol. 43, pp. 1198-1201 (Year: 1995).

Anonymous: "Establishing Instrumental color difference tolerances for your products", Jan. 1, 2008 (Jan. 1, 2008), pp. 1-17, XP093085388, Retrieved from the Internet: URL:https://support.hunterlab.com/hc/en-us/article_attachments/201371449 [retrieved on Sep. 25, 2023].

Argos et al.. "A Structureal Model for Maize Zein Proteins," (in J. Biol Chem. vol. 217 (17): pp. 9984-9990, 1982).

CIELAB color space—Wikipedia; https://en.wikipedia.org/wiki/CIELAB_color_space; retrieved Oct. 5, 2019; 9 pages.

Douglas, "What is the difference betwen corn meal& corn gluten meal?", published Jul. 8, 2011, web link: https://healthfully.com/302484-what-is-the-difference-between-corn-meal-corn-gluten-meal.html (Year: 2011).

El-Hawwary et al. "Relation Between Amino Acids Content of Gliadin, Glutenin, and Isoelectric Point of These Proteins in Some Cereal Products", (in Agric. Res. Review 67 (4): 611-618, 1989).

Mao et al. (Amino Acid Composition, Molecular Weight Distribution and Gel Electrophoresis of Walnut (*Juglans regia* L.) Proteins and Protein Fractions, (in Int. J. Mol. Sci. 15, 2003-2014, 2014).

Nielsen et al. "Extraction and Structure Studies on Corn Glutelin Proteins", (in Cereal Chemistry, vol. 47 (5): pp. 501-512, 1970).

REN Ting-ting, et al., "Research on extraction of zein and its functional properties and application", Science and Technology of

(56) References Cited

OTHER PUBLICATIONS

Cereals, Oils and Foods. vol. 22. Issue 3, May 21, 2014. (English Language Abstract).

* cited by examiner

United States Patent US 12,054,515 B2

CORN PROTEIN ISOLATE AND METHODS OF MANUFACTURING SAME

CROSS-REFERENCE

This application is a National Phase entry of International Application No. PCT/US16/024020, filed Mar. 24, 2012, entitled "CORN PROTEIN ISOLATE AND METHODS OF MANUFACTURING SAME", which claims priority to U.S. Patent Application, Ser. No. 62/137,526, filed Mar. 24, 2015, entitled "CORN PROTEIN ISOLATE AND METHODS OF MANUFACTURING SAME", which are hereby incorporated by reference in their entirety.

TECHNICAL FIELD

This disclosure relates to isolated corn protein and methods of isolating corn protein.

BACKGROUND

For over 100 years, corn wet milling has been used to separate corn kernels into products such as starch, protein, fiber and oil. Corn wet milling is a two stage process that includes a steeping process to soften the corn kernel to facilitate the next wet milling process step that results in purified starch and different co-products such as oil, fiber, and protein. Further corn processing methods are now being investigated to further purify the protein co-product for incorporation into food-grade products, specifically. A combination of increasing interest on the part of consumers for protein in their diet and increasing concerns about the cost and availability of animal derived proteins is causing food companies to look increasingly for new sources of protein.

SUMMARY

Aspects of the present invention provide a corn protein isolate, comprising at least about 85 wt % corn protein on a dry basis: an "a*" color value between about −0.5 and 1.5, and a "b*" color value between about 10 and 25; and less than about 1.5% oil on a dry basis.

Other aspects of the present invention provide a method of producing a corn protein isolate, comprising: providing a destarched corn gluten material, and washing the destarched corn gluten material with a solvent comprising water and a water-miscible organic solvent to obtain a corn protein isolate, comprising at least about 85 wt % protein on a dry basis, an "a" color value ranging from about −0.5 and 1.5, and a "b" color value ranging from about 10 and 25, and less than about 1.5% oil on a dry basis.

And yet other aspects of the present invention provide a method of producing a corn protein isolate, comprising providing a corn gluten material comprising at least about 65 wt % protein, destarching the corn gluten material, and washing the destarched corn gluten material with a solvent comprising about 75-100 wt % ethanol or isopropanol to remove non-protein components, and obtaining a corn protein isolate comprising at least about 85 wt % protein on a dry basis.

And yet further aspects of the present invention provide a method of producing a corn protein isolate, comprising providing a destarched corn gluten material, and washing the destarched corn gluten material with a solvent comprising water and a water-miscible organic solvent to obtain a corn protein isolate having at least 85 wt % protein on a dry basis, wherein a total of from about 3 to 40 liters of solvent per kilogram of destarched corn gluten material is used during the washing step.

DETAILED DESCRIPTION

Starting Corn Material

Figure 1:
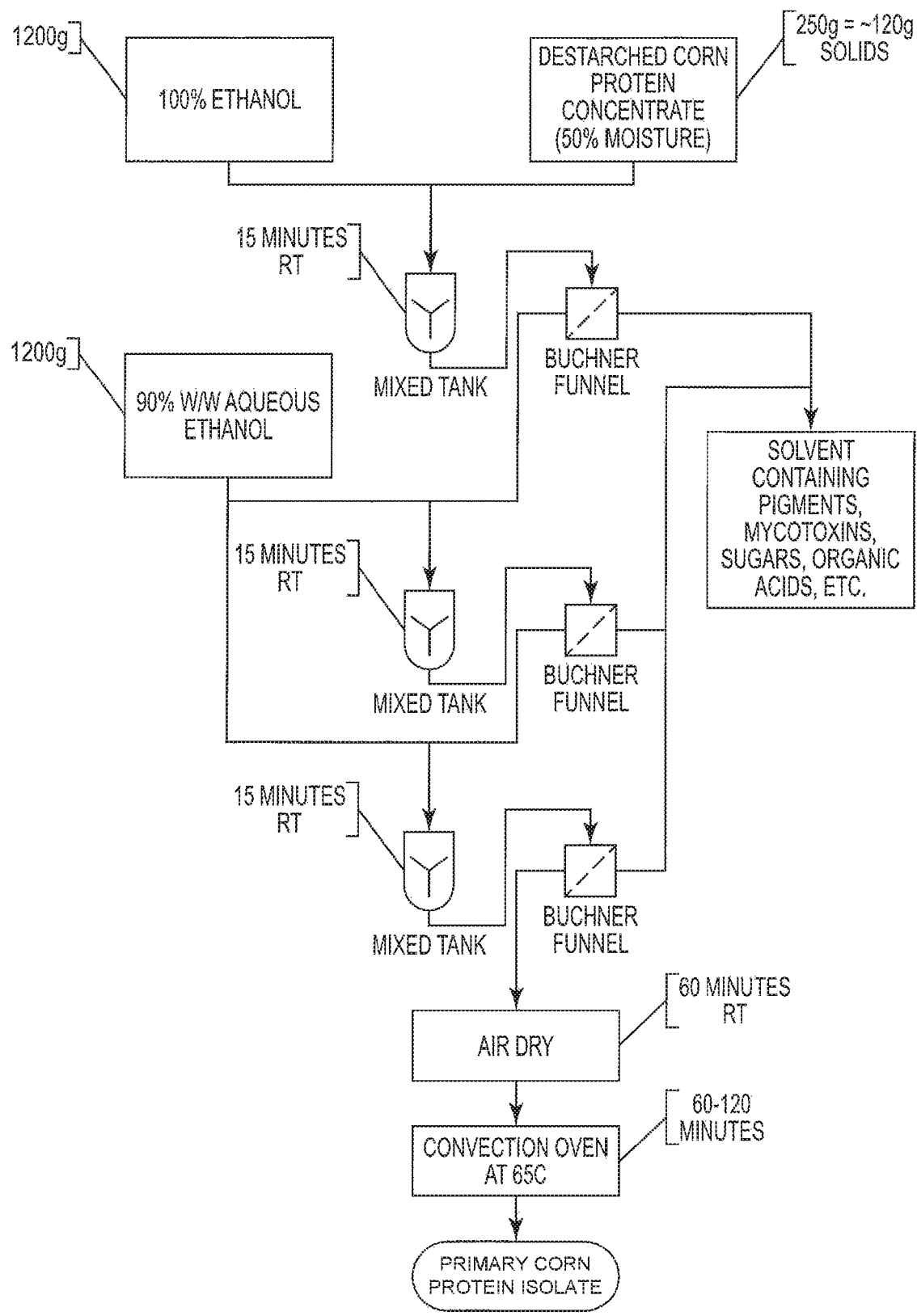
FIG. 1 illustrates an example ethanol solvent washing process using destarched wet corn gluten as the starting material.

The process of producing a corn protein isolate starts with a corn gluten material comprising at least about 65 weight percent (wt %), at least about 70 wt %, or at least about 80 wt % protein on a dry basis (db). In at least certain preferred aspects, the concentration of protein may range from about 65 to 80 wt % (db), about 70 to 80 wt % (db), or about 75 to 80 wt % (db). The concentration of protein throughout this present disclosure is determined by nitrogen concentration as provided in the eighth paragraph under the sub-section of Experimental Procedure and Analytical Methods in the section of Examples.

In preferred aspects, the starting corn gluten material is also destarched. "Destarched" refers to the starting corn gluten material having a residual insoluble starch solids in the range from about 0.1 wt % to 3.0 wt % (ds), as measured by Ewers' Polarimetric method ISO 10520:1997. In at least certain preferred aspects, the residual starch solids in such starting corn gluten material may be in the range from about 0.1 to 2.0 wt % (ds), about 0.1 to 1.0 wt % (ds), or about 0.1 to 0.75 wt % (ds). However, if a corn gluten material is not destarched, the corn gluten material may undergo enzyme or chemical hydrolysis and a subsequent separation step to hydrolyze and remove, respectively, the majority of starch components contained in the corn gluten material.

In some aspects, a starting corn gluten material may be the corn protein concentrate described in U.S. Pat. No. 9,226, 515. A typical analysis of such corn protein concentrate (e.g., Empyreal R 75, Cargill, Incorporated, Wayzata, MN) comprises about 75% to 80% protein, about 4.5% fat, about 5% soluble carbohydrates, and other nutrients (as-is basis), and has a bright yellow or gold color. Such corn protein concentrate may be introduced in dried "cake" form or in wet "cake" form (comprising about 40-60% moisture).

Solvent Washing Process

The starting destarched corn gluten material may then be washed with a water-miscible solvent. In aspects of the present invention, the concentration of the water-miscible solvent may range from about 75 to about 100 wt % or from about 85 to 100 wt %. In preferred aspects, the water-miscible solvent may be an ethanol-containing or isopropanol-containing solvent, or mixtures thereof, in concentrations of about 75 to 95 wt %, or from about 85 to 95 wt %, or about 90 wt %.

A series of solvent washing steps may be performed. A benefit to the processes described herein is the reduction in solvent use compared to other purification processes described in the prior art. In the processes described herein, about 3 to 40 liters (L) of solvent are used per kilogram (kg) of destarched corn gluten to achieve the desired corn protein isolate purity. Other methods for producing a corn protein product, including a corn protein isolate, require many more washing steps and utilize more solvent than the aspects described herein and fail to eliminate the amount of non-protein components compared to the processes described herein. For at least this reason, the processes described herein are more cost efficient and more effective at eliminating non-protein components than those described in the prior art.

Surprisingly, the solvent washes described herein were found to remove many non-protein components (pigments, mycotoxins, sugars, organic acids, oils, etc.) from the starting corn material, thus enhancing the recovery of the corn protein isolate as described in more detail below.

Referring to FIG. 1, there is shown an example process for solvent washing wherein ethanol is used for the solvent (it shall be understood, however, that the process remains the same for an isopropanol or other water-miscible solvent, and mixtures thereof) and the starting corn protein concentrate material is introduced in destarched, wet cake form. As illustrated, about 250 grams (g) of a destarched corn protein concentrate having about 50% moisture is mixed with 100% ethanol (totaling to about 120 g of solids). It shall be understood that because of the about 50% moisture content in the destarched corn protein concentrate, 100% ethanol is used to balance the water in the first mixing tank to achieve a 90 wt % ethanol-containing solvent. The mixture remains in the mixing tank for about 15 minutes and is then sent to a Buchner funnel to filter out the non-protein component-containing solvent and maintain the protein-enriched stream. It shall be understood that while a batch stir tank extraction is illustrated, such extraction may also be carried out by a continuous stir tank reactor or by percolation or immersion extraction. It shall also be understood that while filtration is used in an aspect of this process, other separation techniques, such as centrifugation or decanting, may be utilized to achieve the separation of the non-protein component-containing solvent from the protein-enriched stream. It shall be understood that the destarched corn protein concentrate may contain 30-60% moisture and the amount of ethanol introduced would be adjusted accordingly to achieve the desired ethanol concentration in the extraction tank. That protein-enriched stream is then introduced to 1200 g of a 90 wt % ethanol-containing solvent and mixed in a mixing tank for another 15 minutes before the non-protein component-containing solvent is removed from the protein-enriched stream using filtration yet again. This solvent washing step is repeated once more before the protein-enriched stream is air dried for about 60 minutes and subsequently dried in a convection oven at about 65° C. for about 60 to 120 minutes before recovering the corn protein isolate product. A minimum of three solvent washing steps at this solvent-to-solids ratio is performed in the process to obtain a corn protein isolate product. To reduce the amount of fresh solvent used in the process, the process can be operated as a counter-current extraction.

Corn Protein Isolate Product

The solvent washing process described above concentrates the corn protein by removal of other non-protein components. Notably, the process described herein produces a corn protein isolate product comprising at least about 85 wt %, at least about 86 wt %, at least about 87 wt %, at least about 88 wt %, at least about 89 wt %, at least about 90 wt %, at least about 91 wt %, or at least about 92 wt %, corn protein on a dry basis (db). By way of non-limiting example, the corn protein isolate product may be in a range from about 85 to 98 wt %, about 86 to 98 wt %, about 87 to 98 wt %, about 88 to 98 wt %, about 89 to 98 wt %, about 90 to 98 wt %, about 91 to 98 wt %, or about 92 to 98 wt %, corn protein on dry basis. In further exemplary aspects, the corn protein isolate product may range from about 88 to 96 wt %, about 89 to 96 wt %, about 90 to 96 wt %, about 91 to 96 wt %, about 92 to 96 wt %, about 88 to 95 wt %, about 88 to 94 wt %, about 88 to 93 wt %, about 88 to 92 wt %, about 88 to 91 wt %, or about 88 to 90 wt %, corn protein on dry basis. For example, in at least certain preferred aspects, the corn protein isolate product may range from about 87 to 92 wt %, such as about 88 to 92 wt %, about 89 to 92 wt %, or about 90 to 92 wt %, corn protein on a dry basis.

The presently described process also removes mycotoxin contaminants, specifically aflatoxin. Aflatoxin and zearalenone are known to bind to the corn protein matrix. The water-miscible solvent has a significant impact on reducing the mycotoxin levels. The corn protein isolate has an aflatoxin level of less than 2.0 part per billion (ppb), less than about 1.5 ppb, less than about 1 ppb, less than about 0.5 ppb, or no detectable presence of aflatoxin: a zearalenone level of less than about 200 ppb, less than about 150 ppb, less than 100 ppb, less than 50 ppb, less than 10 ppb, less than 5 ppb, less than about 1 ppb, less than about 0.5 ppb, less than 0.1 ppb, or no detectable presence of zearalenone: a deoxynivalenol level of less than 1 part per million (ppm), less than about 0.5 ppm, less than about 0.1 ppm, or no detectable presence of deoxynivalenol; and a fumonisin level of less than about 4 ppm, less than about 3 ppm, less than about 2 ppm, less than about 1 ppm, less than about 0.5 ppm, or no detectable presence of fumonisin; and mixtures thereof.

Oil is yet another non-protein component found in the destarched corn starting material. The process described herein decreases the oil content from greater than 4 wt % (db) in the starting destarched corn gluten material to less than about 2 wt % (db), less than about 1 wt % (db), less than 0.5 wt % (db), less than 0.1 wt % (db), or no detectable presence of oil, in the corn protein isolate product. The oil removed from the starting destarched corn gluten material may be up to about 100%, such as, by way of example, about 40 to 100%, about 50 to 100%, about 60 to 100%, about 70 to 100%, about 80 to 100%, about 90 to 100%, or about 95 to about 100%, of the initial concentration.

Soluble carbohydrates can be solubilized with selected water-miscible solvents containing water. The total soluble carbohydrate concentration in the corn protein isolate may be reduced to about 40 gram/kilogram (g/kg) or less, about 30 g/kg or less, about 25 g/kg or less, about 20 g/kg or less, or about 10 g/kg or less. The soluble carbohydrates are composed of glucose, fructose, maltose, maltotriose, and/or a series of soluble glucose polymers comprising four or more glucose units linked with alpha 1,4-glycosidic linkages (also known as DP4+ carbohydrates). In some aspects, DP4+ carbohydrates comprise at least about 65%, at least 70%, at least 80%, or at least 85%, of the total soluble carbohydrate concentration. The soluble carbohydrates removed from the starting destarched corn gluten material may be at least 5%, or at least 10%, with certain solvents. In further exemplary aspects, the soluble carbohydrates (mainly small sugars, e.g., fructose, glucose, maltose and maltotriose) removed from the starting destarched corn gluten material may range from about 5 to 95%, such as about 5 to 90%, about 5 to 80%, about 5 to 70%, about 5 to 60%, about 5 to 50%, about 5 to 40%, about 5 to 30%, about 5-20, or about 5-10%. In yet further exemplary aspects, the soluble carbohydrates removed from the starting destarched corn gluten material may range from about 10 to 65%, about 10 to 60%, about 10 to 55%, about 10 to 50%, about 10 to 40%, about 10 to 30%, or about 10 to 20%.

Selected water-miscible solvents at certain solvent to water ratios can extract certain organic acids. As described herein, organic acids include citric acid, succinic acid, lactate, acetate, glycerol, and proprionate. Steeping of corn gives rise to a variety of organic acids and some remain in the starting corn gluten material for this process. The residual total organic acid concentration (i.e., the total of citric acid, succinic acid, lactate, acetate, glycerol and/or proprionate) in the corn protein isolate product after solvent extraction can range from about 4.25 g/kg or less, 4.0 g/kg or less, about 3.5 g/kg or less, about 3.0 g/kg or less, about 2.5 g/kg or less, about 2.0 g/kg or less, about 1.5 g/kg or less, or about 1.0 g/kg, or about 0.5 g/kg or less. In further exemplary aspects, the residual total organic acid concentration in the corn protein isolate product after solvent extraction may range from about 0.5 to 4.25 g/kg, about 0.5 to 3.5 g/kg, about 0.5 to 3.0 g/kg, about 0.5 to 2.5 g/kg, or about 0.5 to about 2.0 g/kg. In at least certain preferred aspects, the residual total organic acid concentration in the corn protein isolate product after solvent extraction may range from about 0.7 to 4.25 g/kg, or about 0.7 to 3.5 g/kg, or about 0.7 to 2.6 g/kg. The total organic acids removed from the starting destarched corn gluten material may be at least 30%. In further exemplary aspects, the total organic acids removed from the starting destarched corn gluten material may range from about 40 to 100%, such as about 50 to 100%, about 60 to 100%, about 70 to 100%. In yet further exemplary aspects, the total organic acids removed from the starting destarched corn gluten material may range from about 40 to 90%, such as about 50 to 90%, 40 to 80%, 50 to 70%, 40 to 70%, or 60 to 70%.

The starting corn material may be yellowish-orange in color because most of the corn pigments (luteins, zeaxanthins, cryptoxanthins, and carotenes) concentrate into the protein stream. Corn pigments are known to be fat soluble and have strong affinity to bind to zein protein. Xanthophylls (luteins, zeaxanthins and cryptoxanthins) make up to 94% of total pigment amounts of the starting corn gluten material. This color is undesirable for most food-grade applications. Accordingly, the solvent washing step described herein eliminates a substantial amount of the color and provides a corn protein isolate product having an "a*" color value in a range from about −0.05 to 1.5, about −0.6 to 0.5, about −0.5 to 0.5, about −0.4 to 0.5, about −0.3 to 0.5, about −0.2 to 0.5, or about −0.1 to 0.5. In further exemplary aspects, the "a*" color value may be in a range from about −0.6 to 0.3, about −0.5 to 0.3, about −0.4 to about 0.3, about −0.3 to 0.3, about −0.2 to 0.3, or about −0.1 to 0.3. For example, in at least certain preferred aspects, the "a*" value may range from about −0.6 to −0.1, about −0.6 to −0.2, about −0.5 to −0.1, or about −0.5 to −0.2. Further, the corn protein isolate product may have a "b*" color value in a range from about 10 to about 25, about 10 to 22, or about 10 to 20. For example, in at least certain preferred aspects, the "b*" value may range from about 10 to 16, about 10 to 15, about 10 to 14, or about 10 to 13. Further, the corn protein isolate product may have a "L*" color value ranging from about 88 and 95, about 89 to 95, or about 90 to 95. For example, in at least certain preferred aspects, the "L*" color value may range from about 88 to 92, about 89 to 92, or about 90 to 92. The color values provided herein correspond to a corn protein isolate product that is off-white in appearance.

EXAMPLES

Experimental Procedure and Analytical Methods

Destarched corn gluten in wet cake form prepared according to U.S. Pat. No. 9,226,515, was collected from a filter dewatering drum after liquefaction and rinsing, chilled and portioned into plastic bags and frozen until use. The wet cake moisture was 53.7%.

Destarched corn gluten, prepared according to U.S. Pat. No. 9,226,515 and collected as described above, was freeze-dried over a five day period to yield a "dry" product containing 2.2% moisture. This was stored at room temperature.

The hexane (BDH, 98.5%), ethyl acetate (ACROS, 99.5%) and isopropanol (Omnisolve and JT Baker, 99.5%) solvents used were analytical grade, while the ethanol solvent (200-proof, Brenntag) was food-grade.

The experiments used the following procedure when wet destarched corn gluten cake was the starting material (also illustrated in FIG. 1). 250 g of destarched corn gluten wet cake was suspended in 1200 g solvent. The cake's moisture was approximately 53.7% moisture, so initial solids were 115 to 116 g. After a brief dispersion with an immersion blender, the suspension was stirred for 15 minutes at ambient temperature (21-24° C.). The solids were collected by filtering the suspension through VWR 417 paper (18.5 centimeter (cm)) on a Buchner funnel. The solids were resuspended in 1200 g of fresh solvent (10% w/w water with 90% w/w indicated solvent) and processed as above for an additional two times. Consequently, the final material was extracted 3 times for a total solvent-to-solids ratio of 30 (disregarding the retained solvent in the final cake). The sample was air-dried in the hood for about 90 minutes at ambient temperature, and then dried at 65° C. for about 75 minutes. This preparation demonstrates the effect of aqueous solvent on final composition.

Figure 2:
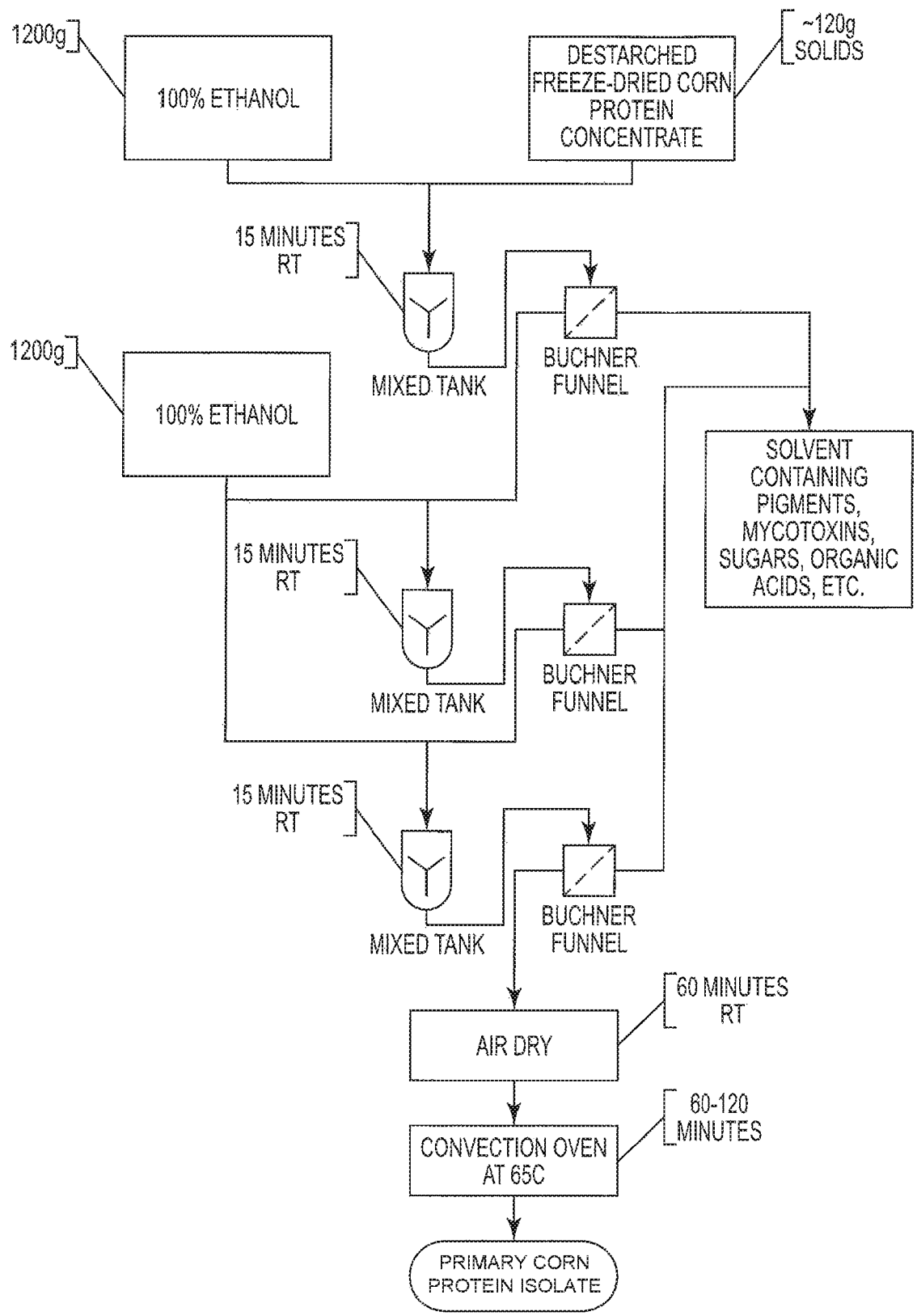
FIG. 2 illustrates an example ethanol solvent washing process using destarched dried corn gluten as the starting material.

The experiments used the following procedure when freeze-dried (FD) destarched corn gluten cake was the starting material (also illustrated in FIG. 2). 125 g of freeze dried destarched corn gluten cake (approximate moisture=2.2%) was measured and dispersed in 1200 g solvent with an immersion blender. The suspension was stirred for 15 minutes before collecting solids by filtering the suspension through VWR 417 paper (18.5 cm) on a Buchner funnel. The solids were re-suspended in 1200 g of fresh solvent and processed as above two more times. Consequently, the final material was extracted 3 times for a total solvent to solids ratio of about 30 (disregarding the retained solvent in the final cake). The sample was air-dried in the hood for about 90 minutes, and then dried at 65° C. for about 75 minutes. This preparation demonstrates the effect of anhydrous solvent on final composition.

Table 1 shows four solvents in anhydrous and aqueous conditions in the final solvent wash (and assumes that anhydrous solvent removes "free" water in earlier washes).

TABLE 1

| Sample | Starting material | Final solvent |
| --- | --- | --- |
| Sample #1 | Wet destarched corn gluten cake | 90 wt % hexane |
| Sample #2 | FD destarched corn gluten cake | 100 wt % hexane |
| Sample #3 | FD destarched corn gluten cake | 100 wt % ethanol |
| Sample #4 | Wet destarched corn gluten cake | 90 wt % ethanol |
| Sample #5 | Wet destarched corn gluten cake | 90 wt % ethyl acetate |
| Sample #6 | Wet destarched corn gluten cake | 90 wt % isopropanol |
| Sample #7 | FD destarched corn gluten cake | 100 wt % isopropanol |
| Sample #8 | FD destarched corn gluten cake | 100 wt % ethyl acetate |

Prior to any analytical analysis, the samples were ground using a SPEX CertiPrep 6870 Freezer/Mill® unit for cryogenically grinding (SPEX SamplePrep, Metuchen, NJ). This unit is an impact grinder cooled by liquid nitrogen. The low temperature provided by the liquid nitrogen aids in minimizing potential lipid oxidation resulting from the grinding process. About 50 g of each sample, embrittled by cold, was pulverized by the hammering of a steel impactor against the end plugs of the sample chamber. The grinder sample program used 5 run cycles, with a pre cool ($T_3$) for 1.0 minute, run time ($T_1$) of 3.0 minutes, and cool time ($T_2$) of 1.0 minute. The impact frequency was 10 per second. The pulverized sample was then collected and stored in appropriate individual containers until needed.

Total crude protein was measured by a TruMac® analyzer (Model 630-300-300, LECO Corporation, St. Joseph, MI) using 6.25 as a nitrogen-to-protein conversion factor. Total crude fat was extracted using a SPEX-Mill 8000M (SPEX SamplePrep, Metuchen, NJ) and weighed. Moisture content was measured using a Mettler-Toledo halogen moisture analyzer (Model HB43-S).

Color was measured using a HunterLab Colorimeter (Model CFE2, Hunter Associates Laboratory, Inc., Reston, VA). The instrument reads out in the Hunter L*, "a*", "b*" scale where the L* value is an indication of color lightness (the higher the value, the lighter/whiter the product). Hunter "a*" represents the red-green color spectrum with a positive value indicating a red hue. Hunter "b*" represents the yellow-blue spectrum with a positive value indicating a yellow hue. All measurements were made on dry powders.

Soluble carbohydrates and organic acids were measured using a High Performance Liquid Chromatography (HPLC) system wherein the temperature of column was 60° C.: the flow rate was 0.6 mL/min: the sample volume size was 20 μL/Injection: the solvent was 0.01 N $H_2SO_4$; and the elution time was 25 minutes total. 2 g of the final dry product were mixed with 20 g of Nanopure® deionized water in a Waring blender at 11,000 rpm for 1 minute followed by a centrifugation step at 4,000 rpm for 5 minutes. The supernatant was then filtered through a 0.45 um syringe filter. This filtrate was injected onto the HPLC column (HPX-87 H prepacked column available from Bio-Rad Laboratory) and compared against a standard solution.

Mycotoxins tests, including Aflatoxin (AFLA), Deoxynivalenol (DON), Fumonisin (FUM), and Zearalenone (ZEA) toxins, were performed using the HPLC method with fluorescence detection. AOAC 994.08 was used to test AFLA; JAOAC, Vol. 88, No. 4, 2005, was used to test DON: AOAC 2001.04 was used to test FUM; and JAOAC, Vol. 88, No. 6, 2005, was used to test ZEA.

Free sulfite was measured by the Monier-Williams AOAC 990.28 method. Any reference to "sulfite" described herein means free sulfite.

Example 1: Experimental Results

The experimental procedure or process described in the first five paragraphs under the sub-section of Experimental Procedure and Analytical Methods in the section of Examples and resulted in concentrating the protein by removal of other components, such as oil, carbohydrates, organic acids, and mycotoxins. It shall be understood that while ethanol and isopropanol containing solvents were not necessarily the most effective in removing each of the oil, carbohydrate, organic acid, and mycotoxin (see Tables 3-6), in balancing the success of overall purification, both 90 wt % ethanol and 90 wt % isopropanol containing solvents were surprisingly the most effective.

Table 2 shows different solvents at different concentrations had a significant effect on the protein concentration, with 90 wt % ethanol and 90 wt % isopropanol solvents resulting in the highest protein concentration on a dry basis (db). 100 wt % hexane, 100 wt % ethanol, 100 wt % isopropanol, and 100 wt % ethyl acetate also were effective in concentrating the protein (db), as well as 90 wt % ethyl acetate. It shall be understood that there may be other water-miscible solvents that may be just as effective in concentrating such protein (db).

TABLE 2

Protein Enhancement

| Sample code | Final solvent | Protein % db |
|---|---|---|
| Sample #1 | 90 wt % hexane | 85.2 |
| Sample #2 | 100 wt % hexane | 89.4 |
| Sample #3 | 100 wt % ethanol | 92.0 |
| Sample #4 | 90 wt % ethanol | 95.5 |
| Sample #5 | 90 wt % ethyl acetate | 88.5 |
| Sample #6 | 90 wt % isopropanol | 92.7 |
| Sample #7 | 100 wt % isopropanol | 89.6 |
| Sample #8 | 100 wt % ethyl acetate | 90.1 |
| FD destarched corn gluten (starting material) | Untreated | 85.1 |

The solvent washing process removed non-protein component such as mycotoxins. The different solvents had a significant effect on the mycotoxin concentration (Table 3). Some solvents did not extract any mycotoxin, while some solvents were partially capable of removing these compounds. The best results were obtained when the solvent concentration was about 90 wt % water-miscible organic constituent and 10 wt % water (in particular, ethanol, isopropanol, and ethyl acetate). For example, 90 wt % ethanol removed all aflatoxin and zearalenone contaminants, and about 75% fumonisin: 90 wt % isopropanol removed all aflatoxin and zearalenone contaminants, and about 30% fumonisin; and 90 wt % ethyl acetate removed all aflatoxin and about 70% zearalenone contaminants. The solvent 100 wt % ethanol also was effective at removing some mycotoxins, about 50% aflatoxin and about 75% zearalenone contaminants.

TABLE 3

Mycotoxin Removal

| Sample code | Final solvent | Aflatoxin (ppb) | Zearalenone (ppb) | Deoxynivalenol (ppm) | Fumonisin (ppm) |
|---|---|---|---|---|---|
| Sample #1 | 90 wt % hexane | 2.2 | 253 | 0.0 | 3.9 |
| Sample #2 | 100 wt % hexane | 2.4 | 279 | 0.0 | 5.4 |
| Sample #3 | 100 wt % ethanol | 1.0 | 54 | 0.0 | 4.7 |
| Sample #4 | 90 wt % ethanol | 0.0 | 0.0 | 0.0 | 1.0 |
| Sample #5 | 90 wt % ethyl acetate | 0.0 | 69 | 0.0 | 4.4 |
| Sample #6 | 90 wt % isopropanol | 0.0 | 0.0 | 0.0 | 3.0 |
| Sample #7 | 100 wt % isopropanol | 2.4 | 259 | 0.0 | 4.5 |

TABLE 3-continued

Mycotoxin Removal

| Sample code | Final solvent | Aflatoxin (ppb) | Zearalenone (ppb) | Deoxynivalenol (ppm) | Fumonisin (ppm) |
|---|---|---|---|---|---|
| Sample #8 | 100 wt % ethyl acetate | 2.2 | 276 | 0.0 | 5.2 |
| FD destarched corn gluten (starting material) | Untreated | 2.1 | 252 | 0.0 | 4.4 |

Much of the protein concentration increase may be attributed to oil removal. The effect of various solvents on oil removal is in Table 4. All solvents tested removed oil, some more effectively than others. The solvent washing process using 90 wt % ethanol, 90 wt % isopropanol, 100 wt % ethanol, 100 wt % isopropanol, 100% ethyl acetate, or 100% hexane, or mixtures thereof, effectively removed at least 90% oil in the corn protein isolate product. 90 wt % ethyl acetate (Sample #5) removed at least or about 40% oil from the corn protein isolate product.

TABLE 4

Oil Removal

| Sample code | Final solvent | Oil % db |
|---|---|---|
| Sample #1 | 90 wt % hexane | 4.29 |
| Sample #2 | 100 wt % hexane | 0.43 |
| Sample #3 | 100 wt % ethanol | 0.16 |
| Sample #4 | 90 wt % ethanol | 0.49 |
| Sample #5 | 90 wt % ethyl acetate | 1.42 |
| Sample #6 | 90 wt % isopropanol | 0.18 |

TABLE 4-continued

Oil Removal

| Sample code | Final solvent | Oil % db |
|---|---|---|
| Sample #7 | 100 wt % isopropanol | 0.47 |
| Sample #8 | 100 wt % ethyl acetate | 0.53 |
| FD destarched corn gluten (Raw material) | Untreated | 5.36 |

The solvent washing process also removed carbohydrates to enhance the protein content (Table 5). Carbohydrates are a class of compounds that can be expected to dissolve differently in solvents of differing polarity, and thus have different results on protein purity. Extraction with 90% ethanol resulted in the lowest soluble carbohydrate residue, with residual carbohydrate at about 21 g/kg of the corn protein isolate product (in other words, about 52% carbohydrates are removed from the starting material when 90% ethanol was used). 90% ethyl acetate and 90% isopropanol were less effective than 90% ethanol, though they did remove about 30% carbohydrates from the starting material. Other aqueous organic solvents were not very effective in removing the saccharides.

TABLE 5

Carbohydrate Removal

| Sample code | Final solvent | Soluble Carbohydrates (g/kg) | | | | | |
|---|---|---|---|---|---|---|---|
| | | DP4+ | Maltotriose | Maltose | Glucose | Fructose | Total |
| Sample #1 | 90 wt % hexane | 18.8 | 5.4 | 6.3 | 8.7 | 4.6 | 43.8 |
| Sample #2 | 100 wt % hexane | 21.1 | 6.0 | 6.9 | 10.0 | 5.1 | 49.0 |
| Sample #3 | 100 wt % ethanol | 22.4 | 5.4 | 5.2 | 4.7 | 2.5 | 40.3 |
| Sample #4 | 90 wt % ethanol | 17.4 | 0.0 | 1.3 | 1.1 | 0.8 | 20.6 |
| Sample #5 | 90 wt % ethyl acetate | 11.5 | 4.8 | 5.1 | 6.7 | 3.4 | 31.4 |
| Sample #6 | 90 wt % isopropanol | 22.3 | 3.6 | 2.7 | 2.4 | 1.4 | 32.3 |
| Sample #7 | 100 wt % isopropanol | 20.6 | 6.0 | 6.9 | 9.8 | 5.3 | 48.6 |
| Sample #8 | 100 wt % ethyl acetate | 20.6 | 6.0 | 7.0 | 9.7 | 5.5 | 48.8 |
| FD destarched corn gluten (starting material) | Untreated | 19.0 | 5.5 | 6.4 | 9.1 | 5.2 | 45.2 |

Yet another way to increase protein concentration is to remove organic acids which also dissolve in solvents as a function of the solvent polarity. The organic acids tested included citric acid, succinic acid, lactic acid, and acetic acid. Table 6 shows organic acid removal. Extraction with 90 wt % ethanol resulted in the lowest total organic acid residue of 3.5 g/kg (or about 70% removal). Extraction with 90 wt % isopropanol resulted in a total organic acid residue of 4.25 g/kg (or about 64% removal) and extraction with 100 wt % ethanol resulted in a total organic acid residue of 5.05 g/kg (or about 57% removal). Other aqueous organic solvents were not as effective in removing the organic acids, though using 90 wt % ethyl acetate resulted in a total organic acid residue of 9.48 (or about 20% removal); using 90 wt % hexane resulted in a total organic acid residue of 10.45 (or about 11% removal); and using 100 wt % hexane resulted in a total organic acid residue of 11.04 (or about 6% removal).

TABLE 6

Organic Acid Removal

| Sample code | Final solvent | Organic Acids (g/kg) | | | | |
|---|---|---|---|---|---|---|
| | | Citric | Succinic | Lactate | Acetate | Total |
| Sample #1 | 90 wt % hexane | 1.62 | 0.98 | 7.34 | 0.51 | 10.45 |
| Sample #2 | 100 wt % hexane | 1.88 | 1.24 | 7.21 | 0.71 | 11.04 |
| Sample #3 | 100 wt % ethanol | 1.84 | 0 | 3.21 | 0 | 5.05 |
| Sample #4 | 90 wt % ethanol | 1.73 | 0.59 | 1.18 | 0 | 3.5 |
| Sample #5 | 90 wt % ethyl acetate | 1.4 | 0.8 | 4.27 | 3.01 | 9.48 |
| Sample #6 | 90 wt % isopropanol | 1.84 | 0.45 | 1.96 | 0 | 4.25 |
| Sample #7 | 100 wt % isopropanol | 2.22 | 2.51 | 7.54 | 1.56 | 13.83 |
| Sample #8 | 100 wt % ethyl acetate | 2.52 | 1.76 | 7.35 | 1.86 | 13.22 |
| FD destarched corn gluten (starting material) | Untreated | 1.99 | 1.75 | 6.99 | 1.02 | 11.75 |

An important feature of a food-grade corn protein isolate is color. The solvent washing process removes pigments (typically yellow-orange in color) from the starting material. Table 7 shows the effect of different solvents on the color, with 90 wt % ethanol and 90 wt % isopropanol demonstrating a substantial removal of pigments from the starting material. These solvents had the greatest effect on removing the yellow and red color from the protein (from an a* value of 4.9 down to 0.0 using 90 wt % ethanol and 0.3 using 90 wt % isopropanol; and from a b* value of 23.8 down to 12.7 using 90 wt % ethanol and 14.4 using 90 wt % isopropanol). 90 wt % ethanol and 90 wt % isopropanol had the highest L* values (the higher the value, the lighter/whiter the product), which corresponds to those samples having an off-white color. The other solvents, except 90 wt % hexane, were also effective at removing the pigments from the starting material, though not as effectively as 90 wt % ethanol and 90 wt % isopropanol.

TABLE 7

| Sample code | Final solvent | Color | | |
|---|---|---|---|---|
| | | L* | a* | b* |
| Sample #1 | 90 wt % hexane | 84.8 | 5.9 | 40.7 |
| Sample #2 | 100 wt % hexane | 89.1 | 2.7 | 30.9 |
| Sample #3 | 100 wt % ethanol | 91.4 | 1.0 | 20.1 |
| Sample #4 | 90 wt % ethanol | 92.2 | 0.0 | 12.7 |
| Sample #5 | 90 wt % ethyl acetate | 79.5 | 6.7 | 39.2 |
| Sample #6 | 90 wt % isopropanol | 91.8 | 0.3 | 14.4 |
| Sample #7 | 100 wt % isopropanol | 89.8 | 2.4 | 26.1 |
| Sample #8 | 100 wt % ethyl acetate | 90.3 | 1.9 | 23.8 |
| FD destarched corn gluten (starting material) | Untreated | 87.3 | 4.9 | 39.5 |

Example 2: Process Using Batch Stir Tank Extraction & Filtration

A number of factors go into considering the efficiency of a process. For example, the more steps that a process requires, the greater the capital cost of building the process and the greater the operating cost for the equipment. Similarly, more steps may translate into longer operating times which is reflected in the higher cost of production as expressed in throughput (kg/hr). In this example using Sample #4, the extraction is completed in three washing steps utilizing a total of about 38 L/kg of solvent as demonstrated in Table 8.

TABLE 8

| Batch Stir Tank | | | |
|---|---|---|---|
| Step | Solvent | L/kg | Time (min) |
| 0 | carry over water from the wet cake | 1 | 0 |
| 1 | 100% ethanol | 12.7 | 25 |
| 2 | 90% w/w ethanol | 12.2 | 25 |
| 3 | 90% w/w ethanol | 12.2 | 25 |
| | Total water volume | 1 | |
| | Total Ethanol volume | 37.1 | |
| | Total time | | 75 |

In an industrial process, the solvent would be recovered and reused, so lower volume of solvent and higher concentration of ethanol in the solvent leads to lower cost of recovery.

Example 3: Process Using Immersion Extraction & Filtration 20 kg of a starting destarched corn gluten cake with 55-60% moisture was processed through a dual rotor crusher with a 0.125-inch screen to generate a uniformly sized particle for homogeneous extraction. The cake was fed to a Crown Iron Works Model IV immersion extractor using a drag conveyor dropping through a rotary valve (for a better understanding, an illustration of the Crown Iron Works Model IV immersion extractor may be found on the crown-iron.com website). The extractor included a series of inclined drag conveyors arranged so that the lower end of the conveyor was submerged in the extraction solvent and the upper end was above the solvent. The conveyor carried the solids forward such that the material was initially submerged in solvent and then the material emerged from the solvent and excess solvent drained back into the solvent stream. At the end of the conveyor, the solids dropped onto another conveyor with a similar arrangement. The model IV extractor had six extraction stages. Fresh solvent was introduced at the discharge end and flowed towards the inlet end and was ultimately discharged at a point preceding the solids introduction. After the final solvent contact, the solids were conveyed up a long section to allow more extensive draining before falling into a conveyor for transport to desolventizing. The solids were fed into the system at 0.45 kg/min and the solvent (100% w/w) was introduced at 1.8 kg/min (based on a volumetric feeder) and the solvent was maintained at 60° C. by in situ heat exchangers. Total solvent to solids ratio was about 4 and total contact time was about 60 minutes. The water of the extraction system was introduced through a combination of carry over water from the input material and water in the fresh solvent. When ethanol was used as a solvent, the composition of the feed solvent to contact the extracted destarched corn gluten was approximately 90% ethanol and 10% water.

Desolventizing occurred in a Bepex Solidaire dryer operated with a surface temperature of about 155-160° C. and an absolute pressure from about 60 to 120 millibar (with a target of about 100 millibar). The resulting product was about 90% solids. The material was ground in a hammer mill to yield a fine powder and had the chemical composition as detailed in Table 9.

TABLE 9

Immersion

| Component | Units | |
|---|---|---|
| Protein | % dry basis | 90.9 |
| Fat | % dry basis | 0.0 |
| Aflatoxin B1 | Ppb | <1 |
| Deoxynivalenol | Ppm | <0.1 |
| Zearalenone | Ppb | <50 |
| Color | L* | 90.5 |
| | a* | −0.39 |
| | b* | 11.9 |

Example 4

Using the process described in Example 3, a number of trials were completed to prepare prototype samples for further analysis. The protein and oil concentrations, and color, in the starting destarched corn gluten material (Emp-010815-2, Emp-032715-2) and in 23 samples of the corn protein isolate product are shown in Table 10A. Table 10B and Table 10C show the soluble carbohydrate and organic acid analyses, respectively, for the same samples.

TABLE 10A

Protein Enhancement, Oil Removal, and Color

| | Protein | Oil | Color | | |
|---|---|---|---|---|---|
| Sample ID | % db | % db | L* | a* | b* |
| Emp-010815-2 | 84.3 | 4.93 | 68.91 | 9.90 | 45.10 |
| Emp-032715-2 | 81.4 | 7.10 | 66.55 | 14.87 | 60.99 |
| CPI-P-012715-10 | 90.9 | 0.00 | 90.48 | −0.39 | 11.85 |
| CPI-P-020215-11 | 89.6 | 0.00 | 91.77 | −0.54 | 10.47 |
| CPI-P-020415-12 | 92.4 | 0.00 | 91.41 | −0.49 | 12.02 |
| CPI-P-020915-14 | 91.6 | 0.04 | 90.85 | −0.46 | 12.21 |
| CPI-P-021115-15 | 91.3 | 0.00 | 90.56 | −0.52 | 12.41 |
| CPI-P 021715-16 | 90.7 | 0.04 | 90.47 | −0.28 | 13.16 |
| CPI-P-021915-17 | 92.3 | 0.01 | 91.06 | −0.37 | 12.96 |
| CPI-P -030215-18 | 92.0 | 0.07 | 90.42 | −0.35 | 13.26 |
| CPI-P-030415-19 | 91.8 | 0.06 | 91.15 | −0.39 | 12.99 |
| CPI-P-030615-20 | 91.4 | 0.09 | 90.55 | −0.27 | 13.25 |
| CPI-P-030915-21 | 92.1 | 0.07 | 90.64 | −0.44 | 10.71 |
| CPI-P-031115-22 | 91.2 | 0.05 | 90.89 | −0.5 | 10.31 |
| CPI-P-031215-23 | 90.6 | 0.08 | 90.84 | −0.4 | 11.44 |
| CPI-P-031315-24 | 91.6 | 0.10 | 91.04 | −0.46 | 11.71 |
| CPI-P-032315-25 | 88.4 | 0.96 | 87.79 | 1.54 | 21.63 |
| CPI-P-032415-26 | 90.6 | 0.33 | 90.18 | −0.06 | 12.72 |
| CPI-P-032515-27 | 90.5 | 0.24 | 90.43 | −0.24 | 11.92 |
| CPI-P-032615-28 | 92.4 | 0.15 | 90.18 | −0.23 | 15.86 |
| CPI-P-032715-29 | 91.9 | 0.00 | 90.70 | −0.36 | 12.58 |
| CPI-P-033015-30 | 91.1 | 0.00 | 91.42 | −0.42 | 13.49 |
| CPI-P-033115-31 | 93.6 | 0.00 | 91.62 | −0.26 | 13.59 |
| CPI-P-040115-32 | 93.0 | 0.06 | 91.62 | −0.19 | 13.31 |
| CPI-P-040215-33 | 90.4 | 0.03 | 91.46 | −0.23 | 13.02 |
| CPI Average (n = 23) | 91.4 | 0.10 | 90.76 | −0.27 | 12.91 |
| CPI Maximum | 93.6 | 0.96 | 91.77 | 1.54 | 21.63 |
| CPI Minimum | 88.4 | 0.00 | 87.79 | −0.54 | 10.31 |

The protein in the corn protein isolate product was in the range of about 88 to 94% (db) with an average of 91.4% (db); the oil in the range of about 0 to 1% (db) with an average of 0.1% (db), which corresponds to about 98 to 99% removal of oil from the starting destarched corn gluten material; and a "L*" color in the range of about 88 to 92 with an average of 90.8; an "a*" color in the range of about −0.5 to 1.5 with an average of −0.3; a "b*" color in the range of about 10 to 22 with an average of 12.9.

TABLE 10B

Carbohydrate Concentrations

Soluble Carbohydrates (CHO) (g per 1 kg of CPI on db)

| Sample ID | DP3+ | Maltotriose | Maltose | Glucose | Fructose | Total |
|---|---|---|---|---|---|---|
| Emp-010815-1 | 7.4 | 2.2 | 3.4 | 0.7 | 0.9 | 14.6 |
| Emp-032715-2 | 8.1 | 1.2 | 0.6 | 0.5 | 0.0 | 10.4 |
| CPI-P-012715-10 | 19.5 | 2.1 | 1.3 | 0.7 | 0.3 | 23.8 |
| CPI-P-020215-11 | 24.0 | 1.6 | 1.0 | 0.7 | 0.0 | 27.3 |
| CPI-P-020415-12 | 18.8 | 2.2 | 1.4 | 0.7 | 0.3 | 23.5 |
| CPI-P-020915-14 | 15.5 | 2.0 | 1.2 | 0.3 | 0.1 | 19.2 |
| CPI-P-021115-15 | 18.5 | 2.2 | 2.2 | 1.4 | 0.5 | 24.9 |
| CPI-P 021715-16 | 21.0 | 2.5 | 1.6 | 0.8 | 0.5 | 26.4 |
| CPI-P-021915-17 | 16.2 | 2.3 | 1.4 | 0.4 | 0.4 | 20.7 |
| CPI-P-030215-18 | 17.8 | 1.9 | 1.1 | 0.5 | 0.2 | 21.5 |
| CPI-P-030415-19 | 17.2 | 1.9 | 1.2 | 0.6 | 0.2 | 21.1 |
| CPI-P-030615-20 | 20.6 | 2.0 | 1.1 | 0.5 | 0.3 | 24.4 |
| CPI-P-030915-21 | 17.7 | 1.4 | 1.0 | 0.3 | 0.1 | 20.4 |
| CPI-P-031115-22 | 11.3 | 1.3 | 0.9 | 0.5 | 0.1 | 14.1 |
| CPI-P-031215-23 | 20.3 | 0.0 | 1.1 | 0.7 | 0.2 | 22.3 |
| CPI-P-031315-24 | 19.2 | 1.3 | 0.9 | 0.6 | 0.1 | 22.2 |
| CPI-P-032315-25 | 26.4 | 3.7 | 3.0 | 2.2 | 1.0 | 36.2 |
| CPI-P-032415-26 | 16.2 | 2.2 | 1.6 | 0.9 | 0.2 | 21.1 |
| CPI-P-032515-27 | 16.4 | 2.2 | 1.5 | 1.0 | 0.5 | 21.6 |
| CPI-P-032615-28 | 16.2 | 2.0 | 1.2 | 0.5 | 0.1 | 20.0 |
| CPI-P-032715-29 | 18.8 | 1.7 | 1.2 | 0.5 | 0.2 | 22.4 |
| CPI-P-033015-30 | 12.5 | 1.0 | 0.6 | 0.3 | 0.0 | 14.3 |
| CPI-P-033115-31 | 6.1 | 0.9 | 0.5 | 0.2 | 0.0 | 7.7 |
| CPI-P-040115-32 | 7.7 | 0.7 | 0.5 | 0.4 | 0.0 | 9.2 |
| CPI-P-040215-33 | 5.4 | 0.5 | 0.3 | 0.2 | 0.0 | 6.5 |
| CPI Average (n = 23) | 16.7 | 1.7 | 1.2 | 0.6 | 0.2 | 20.5 |
| CPI Maximum | 26.2 | 3.7 | 3.0 | 2.2 | 1.0 | 36.2 |
| CPI Minimum | 5.4 | 0 | 0.3 | 0.2 | 0.0 | 6.5 |

It is believed that smaller sugars are removed. The DP4+ carbohydrates are difficult to remove and tend to concentrate in the corn protein isolate product, after other non-protein components are removed using certain water-miscible solvents at certain concentrations. Among the 23 corn protein isolate product samples, three showed about 12% to about 56% removal of total soluble carbohydrates from the starting destarched corn gluten material under the described conditions.

TABLE 10C

Organic Acid Removal

| | Organic Acids (g per 1 kg of CPI on db) | | | | | | |
|---|---|---|---|---|---|---|---|
| | Citric Acid | Succinic Acid | Lactate | Glycerol | Acetate | Propionate | Total |
| Emp-010815-1 | 2.8 | 0.4 | 0.7 | 0.6 | 0.5 | 0.4 | 5.4 |
| Emp-032715-2 | 1 | 0.0 | 0.7 | 0.0 | 1.9 | 0.8 | 4.4 |
| CPI-P-012715-10 | 1.2 | 0.0 | 0.4 | 0.0 | 0.0 | 0.0 | 1.6 |
| CPI-P-020215-11 | 1.3 | 0.0 | 0.2 | 0.0 | 0.0 | 0.1 | 1.6 |
| CPI-P-020415-12 | 1.1 | 0.0 | 0.5 | 0.1 | 0.0 | 0.0 | 1.7 |
| CPI-P-020915-14 | 1 | 0.0 | 0.3 | 0.0 | 0.0 | 0.0 | 1.3 |
| CPI-P-021115-15 | 1.3 | 0.1 | 0.7 | 0.3 | 0.0 | 0.2 | 2.6 |
| CPI-P 021715-16 | 1.4 | 0.0 | 0.4 | 0.3 | 0.0 | 0.0 | 2.1 |
| CPI-P-021915-17 | 1.3 | 0.0 | 0.4 | 0.2 | 0.0 | 0.0 | 1.9 |
| CPI-P-030215-18 | 0.9 | 0.0 | 0.2 | 0.1 | 0.0 | 0.0 | 1.2 |
| CPI-P-030415-19 | 1 | 0.0 | 0.3 | 0.2 | 0.0 | 0.0 | 1.5 |
| CPI-P-030615-20 | 1 | 0.0 | 0.3 | 0.2 | 0.0 | 0.0 | 1.5 |
| CPI-P-030915-21 | 1.2 | 0.0 | 0.3 | 0.0 | 0.0 | 0.0 | 1.5 |
| CPI-P-031115-22 | 1 | 0.0 | 0.2 | 0.0 | 0.0 | 0.0 | 1.2 |
| CPI-P-031215-23 | 1.1 | 0.0 | 0.5 | 0.0 | 0.0 | 0.0 | 1.6 |
| CPI-P-031315-24 | 1.2 | 0.0 | 0.6 | 0.0 | 0.0 | 0.0 | 1.8 |
| CPI-P-032315-25 | 1.5 | 0.0 | 0.0 | 0.0 | 0.0 | 0.0 | 1.5 |
| CPI-P-032415-26 | 1.4 | 0.0 | 0.6 | 0.0 | 0.0 | 0.0 | 2.0 |
| CPI-P-032515-27 | 1.2 | 0.0 | 0.4 | 0.2 | 0.0 | 0.0 | 1.8 |
| CPI-P-032615-28 | 1 | 0.0 | 0.4 | 0.0 | 0.0 | 0.0 | 1.4 |
| CPI-P-032715-29 | 1.1 | 0.0 | 0.3 | 0.0 | 0.0 | 0.0 | 1.4 |
| CPI-P-033015-30 | 0.7 | 0.0 | 0.1 | 0.0 | 0.0 | 0.0 | 0.8 |
| CPI-P-033115-31 | 0.6 | 0.0 | 0.1 | 0.0 | 0.0 | 0.0 | 0.7 |
| CPI-P-040115-32 | 0.8 | 0.0 | 0.3 | 0.0 | 0.0 | 0.0 | 1.1 |
| CPI-P-040215-33 | 0.6 | 0.0 | 0.2 | 0.0 | 0.0 | 0.0 | 0.8 |
| CPI Average | 1.1 | 0.0 | 0.4 | 0.1 | 0.0 | 0.0 | 1.6 |
| CPI Maximum | 1.5 | 0.1 | 0.7 | 0.3 | 0.0 | 0.2 | 2.6 |
| CPI Minimum | 0.6 | 0.0 | 0.0 | 0.0 | 0.0 | 0.0 | 0.7 |

The majority of the residual organic acids comprised citric acid and lactic acid. The total residual organic acid concentration in the corn protein isolate product ranged from about 0.7 to 2.6 g/kg, with an average of less than 2.0 g/kg (i.e., 0.2 wt % (db)). About 60 to 70% organic acids were removed from the starting destarched corn gluten material.

Example 5

A starting destarched corn gluten cake was collected on a rotary drum vacuum filter with rinsing. The destarched corn gluten slurry was fed to the drum at 1.2 gal/min at a density of about 1.016 g/mL. The rinse water, supplemented with 0.3% hydrogen peroxide, was applied at 0.12 gal/min. Upon completion of the vacuum dewatering, the treated cake was frozen until further use.

10 kg of peroxide-treated, destarched corn gluten cake with 60-65% moisture was processed through a dual rotor crusher with a 0.125-inch screen to generate a uniformly sized particle for homogeneous extraction. The cake was fed to a Crown Iron Works Model IV immersion extractor using a drag conveyor dropping through a crossover screw and then a delumper (for a better understanding, an illustration of the Crown Iron Works Model IV immersion extractor may be found on the crowniron.com website) into the extractor. The extractor included a series of inclined drag conveyors arranged so that the lower end of the conveyor was submerged in the extraction solvent and the upper end was above the solvent. The conveyor carried the solids forward such that the material was initially submerged in solvent and then the material emerged from the solvent and excess solvent drained back into the solvent stream. At the end of the conveyor, the solids dropped onto another conveyor with a similar arrangement. The model IV extractor had six extraction stages. Fresh solvent was introduced at the discharge end and flowed towards the inlet end and was ultimately discharged at a point preceding the solids introduction. After the final solvent contact, the solids were conveyed up a long section to allow more extensive draining before falling into a crossover screw for transport to desolventizing. The solvent was fed into the system at 0.109 kg/min and the solids were introduced at 0.027 kg/min (based on a volumetric feeder) and the solvent was maintained at 25° C. by in situ heat exchangers. Total solvent to solids ratio was about 4 and total contact time was about 60 minutes. The water of the extraction system was introduced through a combination of carryover water from the input material and water in the fresh solvent. The composition of the feed solvent to contact the extracted destarched corn gluten was approximately 90% ethanol and 10% water. Consequently, the composition of the solvent varied across the extractor, but the final solvent concentration was about 90% ethanol.

Desolventizing occurred in a Bepex Solidaire dryer operated with a surface temperature of about 155-160° C. and an absolute pressure from about 270-330 millibar (with a target of about 300 millibar).

The resulting product was about 89.0% protein (dry basis). Further, the oil was less than 1% on a dry basis, the product color had "L*" color equal to 90.3, "a*" color equal to 0.2 and "b*" color equal to 16.1. The free sulfite concentration was 104 mg/kg (db) compared to a free sulfite concentration of greater than 500 mg/kg (db) of the destarched corn gluten cake (starting material).

Example 6

A destarched corn gluten cake was collected on a rotary drum vacuum filter with rinsing. The destarched slurry was fed to the drum at 1.2 gal/min at a density of about 1.016 g/mL. The rinse water, supplemented with 0.3% hydrogen peroxide, was applied at 0.12 gal/min. Upon completion of the vacuum dewatering, the treated cake was frozen until further use.

10 kg of peroxide-treated, destarched corn gluten cake with 60-65%% moisture was processed through a dual rotor crusher with a 0.125-inch screen to generate a uniformly sized particle for homogeneous extraction. The cake was fed to a Crown Iron Works Model IV immersion extractor using a drag conveyor through a crossover screw and then a delumper (for a better understanding, an illustration of the Crown Iron Works Model IV immersion extractor may be found on the crowniron.com website) into the extractor. The extractor included a series of inclined drag conveyors arranged so that the lower end of the conveyor was submerged in the extraction solvent and the upper end was above the solvent. The conveyor carried the solids forward such that the material was initially submerged in solvent and then the material emerged from the solvent and excess solvent drained back into the solvent stream. At the end of the conveyor, the solids dropped onto another conveyor with a similar arrangement. The model IV extractor had six extraction stages. Fresh solvent was introduced at the discharge end and flowed towards the inlet end and was ultimately discharged at a point preceding the solids introduction. After the final solvent contact, the solids were conveyed up a long section to allow more extensive draining before falling into a crossover screw for transport to desolventizing. The solvent was fed into the system at 0.218 kg/min and the solids were introduced at 0.027 kg/min (based on a volumetric feeder) and the solvent was maintained at 42.5° C. by in situ heat exchangers. Total solvent to solids ratio was about 8 and total contact time was about 45 minutes. The water of the extraction system was introduced through a combination of carryover water from the input material and water in the fresh solvent. The composition of the feed solvent to contact the extracted destarched corn gluten was approximately 90% ethanol and 10% water. Consequently, the composition of the solvent varied across the extractor, but the final solvent concentration was about 90% ethanol.

Desolventizing occurred in a Bepex Solidaire dryer operated with a surface temperature of about 155-160° C. and an absolute pressure from about 270-330 millibar (with a target of about 300 millibar).

The resulting product was about 95% solids. The material was ground in a hammer mill to yield a fine powder. Further, protein concentration was 87.3% (db), the oil concentration was less than 0.5% (db) and the product color had "L" color equal to 85.9, "a" color equal to 1.5 and "b" color equal to 21.3. The free sulfite concentration was 112 mg/kg (db) compared to a free sulfite concentration averaging about 530 mg/kg (db) of the destarched corn gluten cake (starting material).

Example 7

A starting destarched corn gluten cake was collected on a rotary drum vacuum filter with rinsing. The destarched slurry was fed to the drum at 1.2 gal/min at a density of about 1.016 g/mL. The rinse water, supplemented with 0.3% hydrogen peroxide, was applied at 0.12 gal/min. Upon completion of the vacuum dewatering, the treated cake was frozen until further use.

10 kg of peroxide-treated, destarched corn gluten cake with 60-65% moisture was processed through a dual rotor crusher with a 0.125-inch screen to generate a uniformly sized particle for homogeneous extraction. The cake was fed to a Crown Iron Works Model IV immersion extractor using a drag conveyor dropping through a crossover screw and then a delumper (for a better understanding, an illustration of the Crown Iron Works Model IV immersion extractor may be found on the crowniron.com website) into the extractor. The extractor included a series of inclined drag conveyors arranged so that the lower end of the conveyor was submerged in the extraction solvent and the upper end was above the solvent. The conveyor carried the solids forward such that the material was initially submerged in solvent and then the material emerged from the solvent and excess solvent drained back into the solvent stream. At the end of the conveyor, the solids dropped onto another conveyor with a similar arrangement. The model IV extractor had six extraction stages. Fresh solvent was introduced at the discharge end and flowed towards the inlet end and was ultimately discharged at a point preceding the solids introduction. After the final solvent contact, the solids were conveyed up a long section to allow more extensive draining before falling into a crossover screw for transport to desolventizing. The solvent was fed into the system at 0.218 kg/min and the solids were introduced at 0.027 kg/min (based on a volumetric feeder) and the solvent was maintained at 30° C. by in situ heat exchangers. Total solvent to solids ratio was about 8 and total contact time was about 60 minutes. The water of the extraction system was introduced through a combination of carryover water from the input material and water in the fresh solvent. The composition of the feed solvent to contact the extracted destarched corn gluten was approximately 93.6% ethanol and 6.4% water. Consequently, the composition of the solvent varied across the extractor, but the final solvent concentration was about 93.6% ethanol.

Desolventizing occurred in a Bepex Solidaire dryer operated with a surface temperature of about 155-160° C. and an absolute pressure from about 270-330 millibar (with a target of about 300 millibar).

The resulting product was about 89.0% protein (db). Further, the oil was less than 1% (db), the product color had a "L*" color of 90.3, an "a*" color of 0.2 and a "b*" color of 16.1. The free sulfite was 104 mg/kg (db) compared to a free sulfite concentration averaging about 530 mg/kg (db) of the destarched corn gluten cake (starting material).

The invention claimed is:

1. A method of producing a corn protein isolate, comprising:
    a) providing a destarched wet cake corn gluten material having a moisture content of from about 40 to about 60%;
    b) treating the destarched corn gluten material to separate a solvent containing non-protein components from a protein-enriched stream; and
    c) drying the protein-enriched stream and recovering the corn protein isolate;
    wherein the corn protein isolate:
        i. comprises at least 85 wt % protein on a dry basis;
        ii. has an L* color value of from about 88 to 95, an "a*" color value between about −0.5 and 1.5, and a "b*" color value between about 10 and 25;
        iii. comprises less than about 1.5% oil on a dry basis; and
        iv. has a soluble carbohydrate concentration of 40 g/kg or less;
    wherein the treating consists essentially of washing the destarched corn gluten material with a solvent comprising water and a water-miscible organic solvent selected from the group consisting of ethanol, isopropanol, and mixtures thereof in a water-miscible organic solvent concentration of from about 75 to about 95 wt % in a solvent amount of from about 3 to about 40 liters of solvent per kg of destarched corn gluten material, and separating the resulting protein-enriched stream from the solvent containing non-protein components, which protein-enriched stream is collected as solids by a separation method selected from the group consisting of filtration, centrifugation, and decanting and wherein the treating is carried out a minimum of three times or using an immersion extractor comprising a conveyor and having a minimum of three extraction stages; and
    wherein the destarched corn gluten material is maintained at ambient temperature or in a frozen state from
        the providing of the destarched wet cake corn gluten material in providing step a) until
        initiation of the treatment of the destarched corn gluten material in treating step b).

2. The method of claim 1, wherein the destarched corn gluten material comprises residual insoluble starch solids ranging from about 0.1 to 3.0 wt % on a dry basis, as measured by Ewers' Polarimetric method ISO 10520:1997.

3. The method of claim 1, wherein the washing of the destarched corn gluten material is carried out by washing with a volume of water-miscible organic solvent of from about 3 to about 40 liters per kilogram of destarched corn gluten material having a moisture content of up to 65 wt %.

4. The method of claim 1, wherein the corn protein isolate comprises from about 87 to about 98 wt % protein on a dry basis.

5. The method of claim 1, wherein the corn protein isolate L* color value ranges from about 90 to 92.

6. The method of claim 1, wherein the corn protein isolate comprises less than about 1.0% oil on a dry basis.

7. The method of claim 1, wherein the corn protein isolate has a soluble carbohydrate concentration of 25 g/kg or less.

8. The method of claim 1, wherein the corn protein isolate has an organic acid concentration of about 4.25 g/kg or less.

9. The method of claim 1, wherein the corn protein isolate has an aflatoxin concentration of less than about 1 ppb.

10. The method of claim 1, wherein the corn protein isolate has a free sulfite concentration of less than about 150 ppm.

11. The method of claim 1, wherein the destarched corn gluten material comprises non-protein components selected from the group consisting of organic acids, carbohydrates, mycotoxins, oils and combinations thereof, and the treating removes the non-protein components selected from the group consisting of organic acids, carbohydrates, mycotoxins, oils and combinations thereof.

12. The method of claim 1 wherein the destarched corn gluten material is maintained at ambient temperature
from
the providing of the destarched corn gluten material in providing step a)
until
completion of the treatment of the destarched corn gluten material in treating step b) and before initiation of the drying in drying step c).

13. The method of claim 1 wherein the destarched corn gluten material is maintained at a temperature of from about 21° ° C. to about 24° C.
from
the providing of the destarched corn gluten material in providing step a)
until
initiation of the treatment of the destarched corn gluten material in treating step b).

14. The method of claim 1 wherein the destarched corn gluten material is maintained at a temperature of from about 21° ° C. to about 24° C.
from
the providing of the destarched corn gluten material in providing step a)
until
completion of the treatment of the destarched corn gluten material in treating step b) and before initiation of the drying in drying step c).

* * * * *

UNITED STATES PATENT AND TRADEMARK OFFICE
CERTIFICATE OF CORRECTION

| | | |
|---|---|---|
| PATENT NO. | : 12,054,515 B2 | |
| APPLICATION NO. | : 15/560866 | |
| DATED | : August 6, 2024 | |
| INVENTOR(S) | : Yumin Chen et al. | |

It is certified that error appears in the above-identified patent and that said Letters Patent is hereby corrected as shown below:

In the Specification

In Column 1, Line 41, delete "basis:" and insert -- basis; --, therefor.

In Column 2, Line 44, delete "Empyreal R" and insert -- Empyreal® --, therefor.

In Column 7, Line 20, delete "." and insert -- , --, therefor.

In Column 7, Line 29, delete ":" and insert -- ; --, therefor.

In Column 7, Line 30, delete "min:" and insert -- min; --, therefor.

In Column 7, Line 31, delete "Injection:" and insert -- Injection; --, therefor.

In Column 7, Line 44, delete "DON:" and insert -- DON; --, therefor.

In Column 8, Line 48, delete "fumonisin:" and insert -- fumonisin; --, therefor.

In the Claims

In Column 20, Claim 13, Line 3, delete "21° °C." and insert -- 21° C. --, therefor.

In Column 20, Claim 14, Line 3, delete "21° °C." and insert -- 21° C. --, therefor.

Signed and Sealed this
Fifth Day of November, 2024

Katherine Kelly Vidal
*Director of the United States Patent and Trademark Office*